United States Patent [19]
Kishimoto et al.

[11] 4,116,935
[45] Sep. 26, 1978

[54] ROOM-TEMPERATURE MOISTURE-CURING SILICONE ELASTOMER COMPOSITIONS AND A METHOD FOR THEIR PRODUCTION

[75] Inventors: Keiichi Kishimoto; Masahiko Suzuki, both of Ichihara, Japan

[73] Assignee: Toray Silicone Company, Ltd., Tokyo, Japan

[21] Appl. No.: 817,950

[22] Filed: Jul. 22, 1977

[30] Foreign Application Priority Data

Aug. 20, 1976 [JP] Japan .................................. 51/98738

[51] Int. Cl.$^2$ ............................................. C08G 77/04
[52] U.S. Cl. ................................ 528/34; 260/37 SB; 260/18 S
[58] Field of Search ............. 260/46.5 G, 18 S, 37 SB

[56] References Cited

U.S. PATENT DOCUMENTS

| 3,133,891 | 5/1964 | Ceyzeriat | 260/18 S |
| 3,385,727 | 5/1968 | Thomas | 260/46.5 G |
| 3,692,865 | 9/1972 | Lengick | 260/46.5 G |

*Primary Examiner*—Melvyn I. Marquis
*Attorney, Agent, or Firm*—Robert L. McKellar

[57] ABSTRACT

What is disclosed is a composition of matter which is curable at room-temperature in the presence of moisture which consists of a hydroxylated polyorganosiloxane and a novel cross-linker which is a mixture of an acetoxysilane and an acetoxysiloxane.

4 Claims, No Drawings

ROOM-TEMPERATURE MOISTURE-CURING SILICONE ELASTOMER COMPOSITIONS AND A METHOD FOR THEIR PRODUCTION

THE INVENTION

This invention is related to one-component room-temperature curing silicone elastomer compositions which are cured to a rubberlike state by a reaction with moisture.

Curable, one-component room-temperature silicone elastomers consisting of organopolysiloxanes having hydroxyl groups at the ends and acyloxysilanes as crosslinkers are widely used as sealing agents and adhesives because of their good adhesion and convenience.

However, acyloxysilanes with the formula $RSi(OCOR^1)_3$, where R and $R^1$ are the same or different monovalent hydrocarbon groups, when present in the composition as curing agents, have high melting points and the following problems are generated:

(1) When the acyloxysilane is mixed into the hydroxylated organopolysiloxane, either the acyloxysilane must be heat-melted before the addition or the mixture formed by the addition has to be heated.

(2) When the mixture of hydroxylated polysiloxane and acyloxysilane is stored in tubes or cartridges, the acyloxysilane precipitates resulting in subsequent poor curing.

In order to correct these shortcomings, various methods have been proposed. For example, in Japanese Patent Publication No. 72/17911, the use of a partially hydrolyzed acyloxysiloxane has been proposed.

However, when the acyloxysiloxane is partially hydrolyzed by the addition of water, a condensation polymerization takes place, and acyloxydisiloxane, acyloxytrisiloxane and other more highly polymerized acyloxypolysiloxanes are produced. When such substances are used as curing agents for silicone elastomers, the storage stability is poor, and the substance does not come out of the tube or cartridge easily because of the high viscosity of the composition. This is a great drawback in practical applications.

In this invention, one-component room-temperature curing silicone elastomer compositions, in which the above-described problems have been overcome, and the method for their production are proposed.

This invention is related to a method for the production of room-temperature curing silicone elastomer compositions. These compositions are:

A room-temperature curing silicone elastomer composition consisting of (A) a hydroxylated organopolysiloxane of the general formula HO(RR'SiO)$_n$H 

wherein R and R' are the same or different monovalent hydrocarbon groups, n is at least 5; (B) 0.5–15 weight percent, based on the weight of (A), of a crosslinking material which is a mixture of (I) acetoxysilanes having the general formula $RS:(OAc)_3$ wherein R is the same as above and OAc is the radical

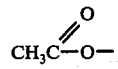

and (ii) acetoxysiloxanes having the general formula $R(AcO)_2SiOSi(OAc)_2R$ wherein R and OAC have the meanings set forth above, wherein the ratio of (i) to (ii) is used in a range of 80–20 weight percent of (i) to 20–80 weight percent of (ii); (C) 0–20 weight percent, based on the weight of (A), of a filler and, (D) 0–5 weight percent based on the weight of (A), of an organometallic compound.

A second kind of room-temperature moisture-curing silicone elastomer compositions consists of (A) a hydroxylated organopolysiloxane expressed by formula $HO(RR^1SiO)_nH$, wherein R and $R^1$ are the same or different monovalent hydrocarbon groups; n is at least 5 and (B) a mixture of an organotriacetoxysilane prepared by a reaction between organotrichlorosilane and acetic acid under air or an inert gas blown into the reactor during the reaction and, a 1,3-diorganotetraacetoxydisiloxane wherein the weight ratio between organotriacetoxysilane and the 1,3-diorganotetraacetoxydisiloxane is within a range of 80–20 weight percent of (i) to 20–80 weight percent of (ii). In the preparation of this type of composition (B) is added to (A) in an amount of 0.5–15 wt% based on the weight of (A).

The hydroxylated polysiloxanes used in this invention are commercially known materials. They are produced by a ring opening polymerization of a cyclic organopolysiloxane expressed by general formula

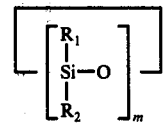

where $R_1$ and $R_2$ are the same or different monovalent hydrocarbons and m is an average value and is an integer in the range of 3–10. The polymerization is caused by heating the cyclic with a basic catalyst such as potassium hydroxide, and subsequent neutralization and purification are carried out under normal procedures. Examples of these type of substances are: polydimethylsiloxane, polymethylphenylsiloxane, polymethylvinylsiloxane, polymethylethylsiloxane, polydiphenylsiloxane. Preferred for this invention are polydimethylsiloxanes or copolymers of them with phenylmethylpolysiloxanes. A monohydroxylated polysiloxane, which has a hydroxyl group only on one end, can be used, in conjunction with the base polymer, for the purpose of adjusting the physical properties of the product. The material for the most part is a linear polysiloxane but inclusion of small amounts of branched polysiloxanes is allowable.

The mixture (B), of organotriacetoxysilanes and 1,3-diorganotetraacetoxydisiloxane can be produced by a one step method, for example, using the method for the production of a mixture of $Si(OCOCH_3)_4$ and $(CH_3COO)_3SiOSi(OCOCH_3)_3$ from $SiCl_4$ which is described in R. N. Kapoor et al., Journal of Indian Chemical Society, 35, 157 (1958) and Chemical Abstracts 53 11080B. In this method, substituting for the $SiCl_4$, an organotrichlorosilane wherein the organic groups can be methyl groups, ethyl groups, propyl groups, vinyl groups, and phenyl groups and reacting with acetic acid under a stream of air or an inert gas gives a mixture of organotriacetoxysilane and 1,3-diorganotetraacetoxydisiloxane. By adjusting the reaction time and temperature, a mixture of organotriacetoxysilane and 1,3-diorganotetraacetoxydisiloxanes is obtained at a desired mixing ratio. However, in order to correct the disadvantages of using organotriacetoxysilane alone, the content of organotriacetoxysilane should be less than 80 wt%. On the other hand, when the content of 1,3-diorganotetraacetoxydisiloxane exceeds 80 wt%, the product obtained by the addition of the mixture of hydroxylated polysiloxane becomes hard and difficult to use.

The mixture of organotriacetoxysilane and 1,3-diorganotetraacetoxydisiloxane should be added to the hydroxylated polysiloxane in an amount within a range of 0.5–15 wt% of the latter. When the amount is larger or smaller than the range given above, poor curing results.

Component C, the filler, may be any commonly used filler for room temperature vulcanizing silicone compositions as long as they do not detract from the advantageous properties. Such fillers can be for example, precipitated and fumed silica, finely divided quartz, diatomaceous earths and the like, alumina and carbon black. The fillers are ordinarily used in an amount of 0–20 weight percent based upon the amount of (A) used in the composition.

Component (D), the organometallic compound can be any of those organometallic compounds which are normally used for curing room temperature vulcanizing silicone compositions based on a curing mechanism of hydroxy, acetoxy and moisture as shown herein. Such materials can be, for example, carboxylates of lead, tin and zinc such as, for example, dibutyltindioctanoate or dibutyltindilaurate.

The component (D) is used in an amount of 0–5 weight percent based on the weight of (A) used in the composition.

It is within the scope of this invention to also include the normal adjuncts, for example, heat-resistance stabilizers, flame retardants, antimicrobial agents, antioxidants and the like.

The compositions of this invention can be stored until use in tubes or cartridges, but they may also be used after being diluted with solvents.

The silicone elastomers of this invention demonstrate excellent adhesion when they are used with metals, glass and synthetic resins. They can be used extensively as the sealing materials, caulking materials and coating materials for buildings, structures, airplanes, ships and automobiles.

This invention will be explained with experimental examples below. "Parts" in these examples means "parts by weight".

CONTROL EXAMPLE 1

(1) Synthesis of methyltriacetoxysilane 450 g. (3 mols) of methyltrichlorosilane and 1285 g. (12.6 mols) of acetic anhydride were placed in a three-neck flask equipped with an agitator, condenser and thermometer and were reacted at 80° C. for an hour under agitation. During the reaction acetyl chloride was produced as a side product and was condensed in the condenser and continuously discharged into a receptacle outside the reaction system.

After terminating the reaction, the remaining acetyl chloride and excess acetic anhydride were removed by distillation at 100° C/20 mm Hg. By continuing the distillation under reduced pressure (5 mm Hg), 572 g. (2.6 mols) of methyltriacetoxysilane with a boiling point of 90°–100° C. were obtained. This will be shown as crosslinking Agent I.

(2) Partial hydrolysis of methyltriacetoxysilane 88 g. (0.4 mol) of methyltriacetoxysilane synthesized by the above-described process and 100 ml. of toluene were placed in a four-neck flask equipped with an agitator, a condenser, a thermometer and a drop funnel. Into this solution a mixed solution of 3.6 g. of water and 20 g. of tetrahydrofuran was gradually added by dropping from the funnel, while the temperature of the reaction solution was being maintained at temperatures below 20° C.

After the addition was completed, the pressure was reduced to 20 mm Hg, and the solution temperature was increased to 150° C., and the toluene, tetrahydrofuran and the acetic acid produced as a by-product were removed.

The results of the gas chromatography on the product confirmed that it was a mixture of 41 wt% methyltriacetoxysilane, 25 wt% 1,3-dimethyltetraacetoxydisiloxane, 18 wt% acetoxytrisiloxane, 10 wt% acetoxytetrasiloxane and 6 wt% unknown substances. This will be shown as cross-linking Agent II.

EXAMPLE 1

(1) Synthesis of a mixture of methyltriacetoxysilane and 1,3-dimethyltetraacetoxydisiloxane.

450 g. (3 mols) of methyltrichlorosilane and 810 g. (13.5 mols) of acetic acid were placed in a four-neck flask equipped with an agitator, a condenser, a thermometer and a nitrogen gas inlet. Then a reaction was carried out at 60° C. for 2 hours while nitrogen gas was blown into the reaction solution at a rate of 1.5 l./hr. Then the reaction was continued for another 2 hours at 80° C. under agitation. Then the pressure was reduced to 20 mm Hg. The excess acetic acid was removed by stripping for an hour at a solution temperature of 100° C. 510 g. of a product was obtained. The gas chromatographic analysis of the product confirmed that it was a mixture of 29 wt% methyltriacetoxysilane and 71 wt% 1,3-dimethyltetraacetoxydisiloxane, and the production of polysiloxanes higher than the dimer was practically negligible. This will be shown as Cross-linking Agent III.

(2) By following the same procedure, methyltrichlorosilane and acetic acid were reacted first for 2 hours at 60° C. and next for 1 hour at 80° C. In this reaction, 500 g. of a mixture in which methyltriacetoxysilane is 50 wt% and 1,3-dimethyltetraacetoxydisiloxane is 50 wt% was obtained. This will be shown as Cross-linking Agent IV.

EXAMPLE 2

Compositions prepared by compounding 100 parts of a 10,000 centipoise polydimethylsiloxane having a hydroxyl group on its terminal ends, 6 parts of Cross-linking Agents I–IV synthesized according to the process previously described, 10 parts of fumed silica with a specific surface area of 200 m$^2$/g and 0.05 parts of dibutyltin dioctanoate were prepared. They were then used to fill aluminum tubes and plastic cartridges for the purpose of making fluidity measurements.

Each composition was pressed out of the tube to form a sheet 2 mm in thickness. It was left in a room maintained at 25° C. and at a relative humidity of 60% for 3 days while curing. Then it was tested for hardness (JIS A), tensile strength and elongation by the methods specified in JIS K-6301.

Next, each composition was subjected to a test of its fluidity at the time when it is pushed out of the cartridge by the method of U.S. Military Specification MIL S 7502C.

The tubes containing various compositions were stored for one month in a refrigerator maintained at −20° C. Then the tubes were cut out to see whether crystals had precipitated. The results of these tests are shown in Table I.

It should be noted that the cross-linking agents of Control Examples I and II were from the prior art.

Table I

|  | Kind of cross-linking Agent | Physical properties after curing | | | Fluidity (kg/min) | Precipitation in the tube |
|---|---|---|---|---|---|---|
|  |  | Hardness (JIS A) | Tensile strength (kg/cm²) | Elongation (%) |  |  |
| Control Example | I | 25 | 21 | 470 | 275 | Yes |
|  | II | 28 | 24 | 410 | 180 | No |
| Example | III | 26 | 21 | 450 | 260 | No |
|  | IV | 26 | 21 | 455 | 265 | No |

That which is claimed is:

1. A room-temperature curing silicone elastomer composition consisting of
    (A) a hydroxylated organopolysiloxane of the general formula HO(RR'SiO)$_n$H wherein R and R' are the same or different monovalent hydrocarbon groups,
    n is at least 5;
    (B) 0.5–15 weight percent, based on the weight of (A), of a crosslinking material which is a mixture of
    (i) acetoxysilanes having the general formula RSi(OAc)$_3$ wherein R is the same as above and OAc is the radical

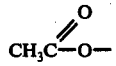

and
    (ii) acetoxysiloxanes having the general formula R(AcO)$_2$SiOSi(OAc)$_2$R wherein R and OAc have the meanings set forth above, wherein the ratio of (i) to (ii) is used in a range of 80–20 weight percent of (i) to 20–80 weight percent of (ii);
    (C) 0–20 weight percent, based on the weight of (A), of a filler and,
    (D) 0–5 weight percent based on the weight of (A), of an organometallic compound.

2. A room-temperature curing silicone elastomer composition as in claim 1 wherein (A) is a hydroxy terminated polydimethylsiloxane and (B) is a mixture of methyltriacetoxysilane and 1,3-dimethyltetraacetoxydisiloxane.

3. A room-temperature curing silicone elastomer composition as in claim 1 wherein (B) (i) is prepared by the reaction of organotrichlorosilane with acetic acid in an inert atmosphere, the product of which is mixed with (ii) 1,3-diorganotetraacetoxydisiloxane in a ratio of 80–20 weight percent of (i) to 20–80 weight percent of (ii) and the mixture (B) is present in the total composition in an amount of 0.5–15 weight percent.

4. A composition as in claim 3 wherein during the preparation of (B) (i), inert air or gas is blown continuously into the reactor containing the organotrichlorosilane and acetic acid.